United States Patent [19]

Subramanian et al.

[11] Patent Number: 5,800,802
[45] Date of Patent: Sep. 1, 1998

[54] CHELATOR IDAC-2

[76] Inventors: Ramaswamy Subramanian, 352 Catoctin Ave., Frederick, Md. 27101; James Colony, 704 N. 75th St., Seattle, Wash. 98103

[21] Appl. No.: 442,856

[22] Filed: May 17, 1995

Related U.S. Application Data

[63] Continuation-in-part of Ser. No. 278,721, Jul. 22, 1994, abandoned, which is a continuation of Ser. No. 92,739, Jul. 16, 1993, abandoned, which is a division of Ser. No. 419,871, Oct. 11, 1989, Pat. No. 5,244,816.

[51] Int. Cl.$^6$ .................. C07F 19/00; C07C 331/28
[52] U.S. Cl. .......... 424/1.49; 424/1.53; 424/1.69; 530/300; 530/350; 534/10; 556/33; 558/17
[58] Field of Search ............... 534/10; 556/33; 558/17; 424/1.49, 1.69, 1.53; 530/300, 350

[56] References Cited

U.S. PATENT DOCUMENTS

| | | | |
|---|---|---|---|
| 5,244,816 | 9/1993 | Subramanian et al. | 436/545 |
| 5,488,126 | 1/1996 | Subramanian et al. | 558/117 |

*Primary Examiner*—Michael G. Ambrose
*Attorney, Agent, or Firm*—William M. Blackstone

[57] ABSTRACT

A method for removing unbound labeling reagent from a composition comprising bound and unbound labeling reagents in which a chelator-matrix conjugate capable of binding unbound labeling reagent is contacted with a biomolecule labeling reaction mixture, by which the unbound labeling reagent is scavenged by the chelator-matrix conjugate, and then the labeled biomolecule essentially free of unbound labeling reagent is removed. Also included is a novel chelator IDAC-2, which may be used for labeling biomolecules and for scavenging in the chelator-matrix conjugate.

7 Claims, 5 Drawing Sheets

1 REACTION VIAL

2 VIAL WITH BEADS

3 PRODUCT VIAL

STEP I RADIOLABELING REACTION

STEP II. REMOVAL OF FREE METAL

STEP III. FILTRATION & FILLING OF PRODUCT VIAL

CHELATOR IDAC-2

This is a continuation-in-part of U.S. patent application Ser. No. 08/278,721, filed Jul. 22, 1994, now abandoned which is a continuation of U.S. patent application Ser. No. 08/092,739, filed Jul. 16, 1993, now abandoned, which is a division of U.S. patent application Ser. No. 07/419,871, filed Oct. 11, 1989, which issued as U.S. Pat. No. 5,244,816 on Sep. 14, 1993.

FIELD OF THE INVENTION

The invention relates to a novel chelator IDAC-2 and to the labeling of biomolecules. The invention particularly relates to the separation of labeled biomolecules from unbound labeling reagent following the labeling reaction. Particular applications of the invention lie in the fields of immunodiagnostics and immunotherapy, as well as use in purification techniques for obtaining protein-metal conjugates free from unbound metal.

BACKGROUND OF THE INVENTION

Biomolecules can be labeled with any of a variety of reagents, including radionuclides, toxins, vitamins, fluorescent compounds and chelating agents. A labeling reagent may be incorporated as a constituent of a biomolecule, for example by metabolic labeling or by nick translation, or may be attached to a biomolecule by a covalent bond or another intermolecular force. Examples of the latter category of labeling methods include the use of isothiocyanate derivatives or fluorochromes to render antibodies fluorescent, the use of photoactive derivatives of biotin to label nucleic acids and the use of oxidative or enzyme-mediated reactions to attach iodine onto proteins at tyrosine residues. The labeling procedure can be as simple as mixing a biomolecule and a labeling reagent together.

U.S. Pat. No. 4,707,352 discloses a labeling method that comprises the step of contacting an unlabeled compound, consisting of a chelating agent conjugated to a biomolecule, with an ion transfer material to which is bound a radiometal. The affinity of said ion transfer material for the radiometal is less than the affinity of said chelating agent for said metal. An example of a column containing an ion exchange resin loaded with $^{63}$Ni is used. A chelator conjugate is passed through the column and is eluted as a radiolabeled chelator conjugate. The components to perform the labeling method may be incorporated into kits.

At the conclusion of a labeling reaction, it is often desirable to purify the labeled biomolecule, the product, by separating any reactant, particularly unreacted labeling reagent, from the product. The presence of unbound labeling reagent can confound outcomes by associating with irrelevant molecules (non-specific binding) or by contributing to the background.

Because many labeling reagents are small molecules or elements, common methods for separating product from unbound reagent rely on size or weight differential. Thus, size exclusion chromatography or dialysis may be used. If there is a charge difference between the product and reactant, ion exchange chromatography is a suitable separation method.

A method for purifying radiolabeled antibody combining both ion exchange and size exclusion resins is disclosed in U.S. Pat. No. 4,454,106. A 9 cm column is made comprising 1 ml of an ion retarding resin above 1 ml of a 200–400 mesh cation exchange resin, which is above 7 ml of gel filtration medium capable of fractionating particles 1,500–25,000 daltons in weight. The column is equilibrated with a buffer consisting of 200 mM sodium chloride and 10 mM MES at pH 6.0. In the related U.S. Pat. No. 4,472,509, the preferred bed for purifying technetium-labeled antibodies is the three component bed described above modified to include 1 ml of an anion exchange resin situated below the cation exchange resin and above the gel filtration medium.

Mukkala et al. (Anal. Biochem (1989) 176:319–325) labeled IgG with $Eu^{3+}$ using bridging chelators. The labeled antibody product was purified from the reactants by passing the reaction mixture over a combined 1.5×30 cm Sephadex G-50 (Pharmacia Fine Chemicals; dextran beads) column and a 1.5×30 cm Trisacryl GF2000 (Reactifs IBF; polyacrylamide beads) column.

Esteban et al. (*J. Nucl. Med.* (1987) 26:861–870) compared four protocols for purifying $^{111}$In-labeled antibody at completion of the labeling procedure. They divided a single labeling preparation into four equal portions. One aliquot was treated with excess EDTA in solution without subsequent separation. Another aliquot was passed over a 1×8 cm gel exclusion (Sephadex G-50 fine) column. The third aliquot was injected onto a 7.5 mm×30 cm HPLC (TSK 3000) column and the final aliquot was treated sequentially over the G50 column and then the TSK 3000 column. The poorest results were obtained with the EDTA treatment, the G-50 column was marginally better, the HPLC-purified labeled antibody had a tumor:liver ratio three times that of the EDTA-purified aliquot and the best results were obtained with the G-50/TSK 3000 combination. The authors concluded that the widely used EDTA method was inefficient for producing clean preparations, and other purification methods should be considered if one wants to minimize background.

U.S. Pat. No. 4,775,638 discloses a single vial technique for radiolabeling antibody. The method comprises introducing radioisotope into a sealed vessel in which the inner surface of said vessel is coated with a catalyst; introducing antibody into said vessel; incubating the mixture; introducing into said vessel an ion exchange resin that absorbs radioisotope not bound to antibody; withdrawing the mixture; and separating the resin from the supernatant. The preferred is an anion exchange resin such as AG 1-X8 (Bio-Rad). Although the method is directed primarily to radio-iodination procedures, the inventor surmised that the catalyst-mediated attachment of radioisotope to antibody and the subsequent purification of said labeled antibody might be adapted for $^{67}$Ga and $^{111}$In labeling by chelation.

Notwithstanding the variety of separation methods available to the artisan, a systematic limitation constrains the use of labeled biomolecules in procedures demanding high sensitivity. That limitation is the sometimes low efficacy of removing unbound labeling reagent of many current methods in the art. A clear example is the use of radiolabeled anti-cancer antibodies in-situ for the detection of malignant growths, a method known as radioimmunoscintigraphy. For various reasons not related directly to the instant invention, often only a small amount of antibody binds to a malignancy. Thus, the signal is difficult to discern even under ideal conditions. It is not uncommon for diagnosis to be rendered impossible because of high background. Accordingly, one way to assure or enhance detection is using labeled antibody that is significantly free from unbound radionuclides.

A further limitation to the use of gel exclusion chromatography for purification is the propensity of IgM antibodies to bind nonspecifically and at times irreversibly to the column matrix. See, for example, Halpern et al., *J. Nucl. Med.* (1988) 29:1688–1696.

Another limitation is related to the prolonged time frame of most procedures. Many of the radionuclides and particularly the radiometals have short half-lives, which is often a matter of hours. Thus, rapid purification can enhance the specific activity of a labeled biomolecule preparation.

Furthermore, the separation procedures recited above are not without additional shortcomings. Many require costly equipment and skilled technicians. Many are prone to biologic contamination, require close monitoring and are not amenable to scale-up. The equipment may also be difficult and costly to decontaminate in the event of radioactive spills.

Resolution of the above-noted problems provided the motivation for the instant invention. Disclosed herein is a means for obtaining a higher degree of separation of labeled product from unbound reactant than achieved using current procedures. The instant method is advantageous for several reasons, including simplicity and inexpensiveness. Additionally the method is not prone to biologic contamination, does not affect the bioactivity of the biomolecule, offers high concentrated yields, can be used in a standard hospital laboratory by nursing staff, is easy to dispose of after use, has a long shelf life and is adaptable for use with a variety of labeling reagents and biomolecules.

SUMMARY OF THE INVENTION

The instant invention relates to a novel chelator IDAC-2 and its use in a method for labeling biomolecules, as well as for separating, after a labeling reaction, labeled biomolecules from any unbound or weakly bound labeling reagent. The invention teaches the use of chelator attached matrices to scavenge said unbound labeling reagent. The method offers several advantages, including simplicity, highly efficient removal of unbound labeling reagent and economy. The novel reagents to carry out the invention are readily adaptable into kit form for use in applied settings, as in hospitals and nuclear pharmacies. IDAC-2 may also be used for binding metals, including radiometals, for other uses, including in-vivo imaging and therapy. Complexes of IDAC-2 with polymers, biomolecules and metals are also part of the invention.

DETAILED DESCRIPTION OF THE INVENTION

Figure 1:
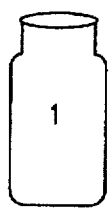
FIG. 1 depicts the use of a plurality of vessels to carry out the method of labeling.
Figure 1:
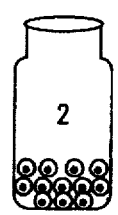
Figure 1:
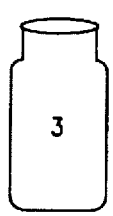
Figure 1:
Figure 1:
Figure 1:
Figure 1:
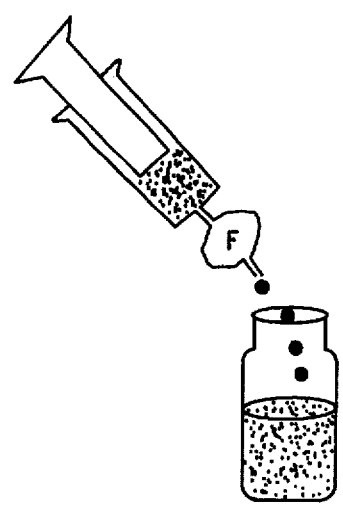

All of the terms used in the specification and the claims are known to one with ordinary skill in the art. Nevertheless, to provide clear and consistent understanding of the specification and claims, including the scope given to such terms, the following definitions are provided:

Biomolecule: Element or compound compatible in or with a biologic entity.

Bound: Physical attachment of labeling reagent to a biomolecule.

Chelator: Reagent that binds metal ions with high affinity. Known also as a chelating agent.

Conjugate: A composite. As a verb, to join.

Derivatize: Modify a parent substance.

Labeling reagent: Substance to be reacted with a biomolecule that confers an additional property on said biomolecule wherein said biomolecule can be detected, tracked or monitored.

Polyaminopolycarboxylate: Compound, used often as a chelating agent, characterized by a plurality of amino groups and a plurality of carboxyl groups.

Product: The resulting substance of a reaction between or among reactants.

Reactant: Ingredient of a reaction, for example, a biomolecule is mixed with a labeling reagent to produce a conjugate, said biomolecule and said labeling reagent are two reactants of that reaction, and said conjugate is the product.

Unbound reactant: Reactant that is not physically attached to another substance.

The invention includes the novel chelator IDAC-2, as well as the use of IDAC-2 conjugated to an inert matrix, preferably a particulate matrix to scavenge unbound labeling reagent. IDAC-2 has a high avidity and high affinity for lower molecular weight compounds, which many labeling regents are. The preferred chelating agent is the novel IDAC-2.

Suitable matrices include glass, polystyrene, amine derivatized polymers, silica, agarose, silica propylamine, copolymers and other resins. With certain matrix-chelator combinations, the attachment of the chelating agent to the matrix does not require a complex reaction. Polystyrene and glass, for example, have an inherent binding capacity for small molecules, proteins and the like. However in the case of amine derivatized polymer beads or amine derivatized polymer-coated glass beads, the chelators can be linked chemically to the beads.

The invention is suitable particularly for procedures that require biomolecules labeled with metals. It is not uncommon for the biomolecules to be labeled using a chelating agent bridge, i.e., the chelating agent is conjugated to the biomolecule, and the conjugate is then loaded with a metal, wherein the metal is bound by the chelating agent. Suitable metals include $\alpha$- and $\beta$-emitting radionuclides, $\gamma$-emitters, x-ray emitters, positron emitters, paramagnetic metal ions, luminescent and fluorescent metals. To further exemplify the range of elements and isotopes that can be used, suitable candidates include $^{56}$Fe, $^{54}$Fe, $^{55}$Co, $^{52}$Fe, $^{43}$Sc, $^{44}$Sc, $^{47}$Sc, $^{123}$I, $^{125}$I, $^{130}$I, $^{131}$I, $^{133}$I, $^{135}$I, $^{86}$Rb, $^{134}$Cs, $^{101}$Rh, $^{203}$Pb, $^{137}$Cs, $^{133}$Ba, $^{88}$Y, $^{90}$Y, $^{152}$Eu, $^{67}$Ga, $^{68}$Ga, $^{51}$Cr, $^{225}$Ac, $^{32}$P, $^{72}$As, $^{153}$Sm, $^{186}$Re, $^{199}$Au, $^{105}$Rh, $^{72}$Se, $^{97}$Ru, $^{100}$Pd, $^{109}$Pd, $^{119}$Sb, $^{128}$Ba, $^{197}$Hg, $^{211}$At, $^{212}$Bi, $^{212}$Pb, $^{213}$Bi, $^{188}$Re, $^{142}$Pr, $^{107}$As, $^{111}$In, $^{67}$Cu, $^{75}$Br, $^{77}$Br, $^{11}$C, $^{14}$C, $^{13}$N $^{15}$O, $^{35}$S, $^{18}$F, Pr, Nd, $^{0159}$Gd, $^{166}$Ho, $^{194}$Ir, Sm, Eu, Gd, Tb, Dy, Ho, Er, Tm, Yb, $^{99m}$Tc, $^{192}$Ir and $^{291}$Am, although it is preferable when using a chelator that the species be a cation.

A particular advantage is realized when the same chelating agent, IDAC-2, is conjugated both to the biomolecule and to the matrix. Because of no difference in affinity, there is little chance that the separation process will remove labeling reagent once bound to the biomolecule.

The labeling procedure can be performed in one or more sealed reaction vessels or in a multiple-chambered single reaction vessel. FIG. 1 diagrams an embodiment requiring multiple vessels, comprising a first reaction vial, a second vial containing chelator attached to a matrix and a third product vial. Radiolabeling occurs in the first vial, the reaction mixture is removed to the second vial, where the mixture contacts the chelator-matrix conjugate, thereafter the supernatant is removed, for example, by means of a syringe, and said supernatant, which may be filtered, is collected in the third vial.

Figure 2:
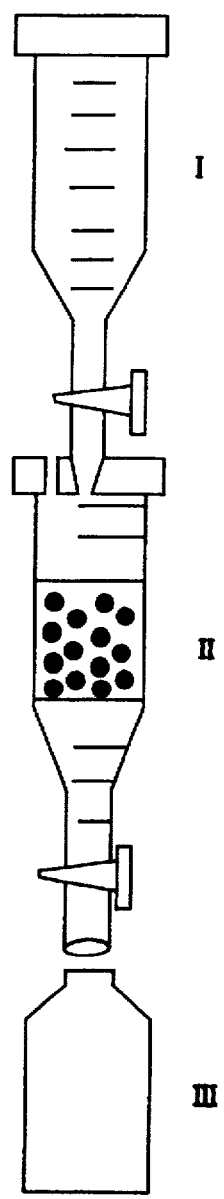
FIG. 2 depicts another embodiment comprising a single vessel with a plurality of compartments.

FIG. 2 illustrates another embodiment in which a single vessel with multiple compartments is represented. Said compartments are separated from each other by means for permitting transfer of a reaction mixture from a first compartment (I) to a second adjacent compartment (II) containing chelator attached to a matrix. In this embodiment a valve device, e.g., a stopcock, separates the compartments. Equivalents of the stopcock include rupturable non-permeable membranes, moveable stoppers and scored glass. A third compartment (III), which receives the reaction mixture after the unbound labeling reagent is removed from the reaction mixture by the chelator-matrix conjugate, may be attached to the second compartment.

A third embodiment uses a sealed two compartment vessel. The labeling reaction is conducted in the first compartment, into which the reactants are introduced, for example, by a syringe. The second compartment contains a chelator-matrix. After the labeling reaction is complete, a stopper means separating the first compartment and the second compartment is breached and the reactants are contacted with the chelator-matrix in the second compartment. After sufficient time for unbound label to be captured by the chelator-matrix, the labeled biomolecule in the supernatant may be removed using a syringe. Because the entire procedure takes place in a sealed, sterile vessel, the supernatant may be administered directly to a patient. The size of the matrix bound to the chelator, e.g., polymer beads, would be selected to be too large to enter the syringe.

Figure 3:
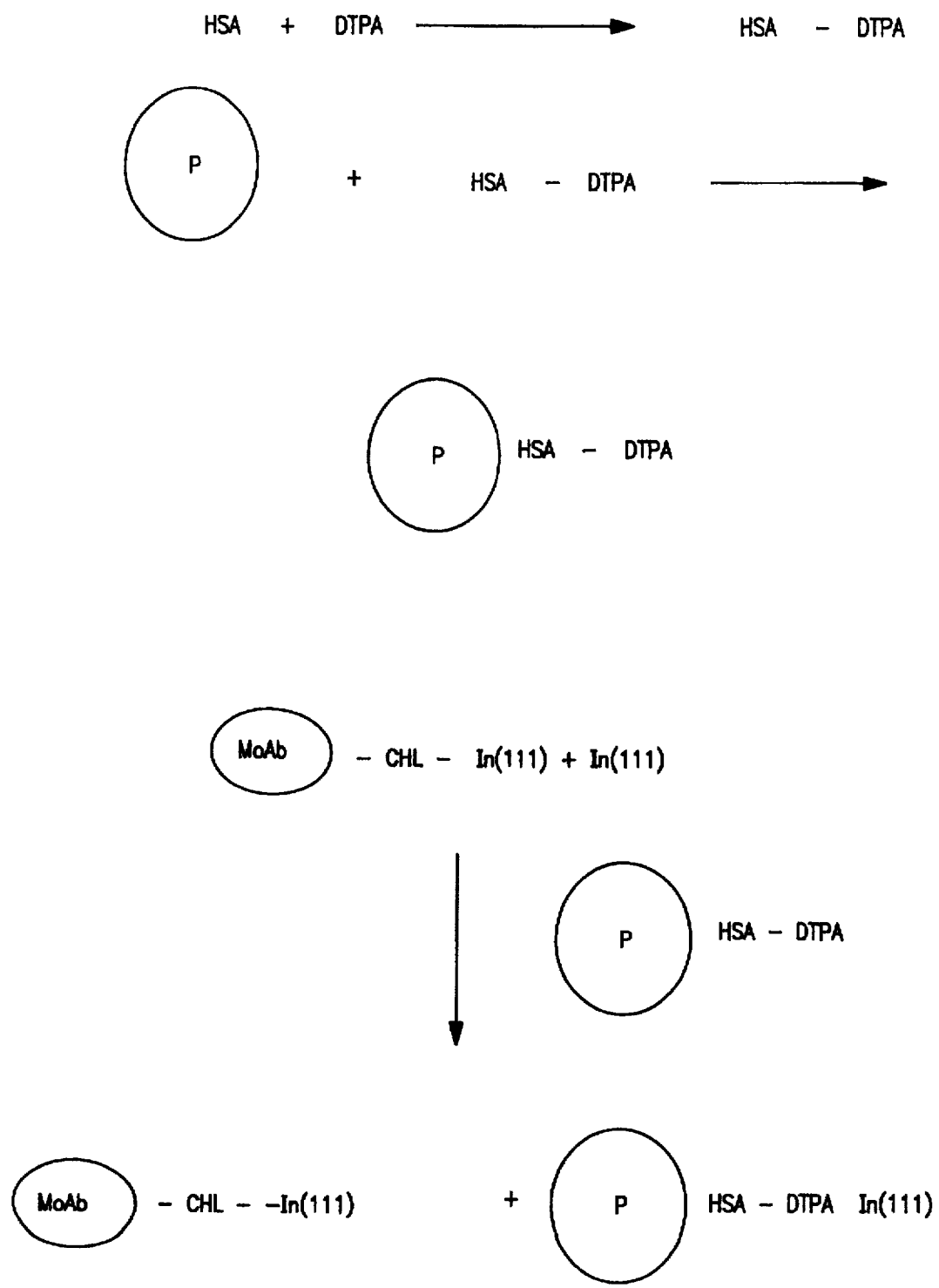
FIG. 3 depicts a method for making chelator attached matrix.

Appropriate matrices are selected and conjugated with a chelating agent. FIG. 3 is an example of preparing beads by indirect coupling. Human serum albumin (HSA) and IDAC-2 are conjugated. The HSA-IDAC-2 conjugate is attached to a particulate polymer matrix (P) to form P-HSA-IDAC-2. In another reaction vial a chelator (CHL), preferably IDAC-2, is conjugated to a monoclonal antibody (MoAb). The MoAb-CHL conjugate is labeled with indium (In(111)). In the figure unbound labeling reagent is denoted as In(111) and labeled antibody as MoAb-CHL-In(111). P-HSA-IDAC-2 is added to the reaction mixture to scavenge In(111) by chelation.

Figure 4:
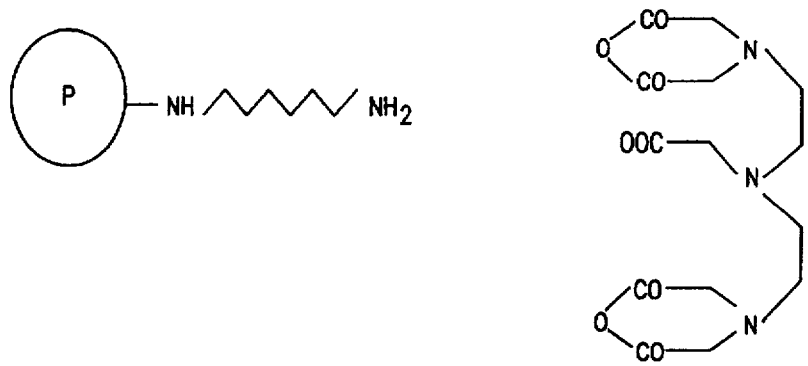
FIG. 4 depicts an alternative method for preparing chelator attached matrix.
Figure 4:
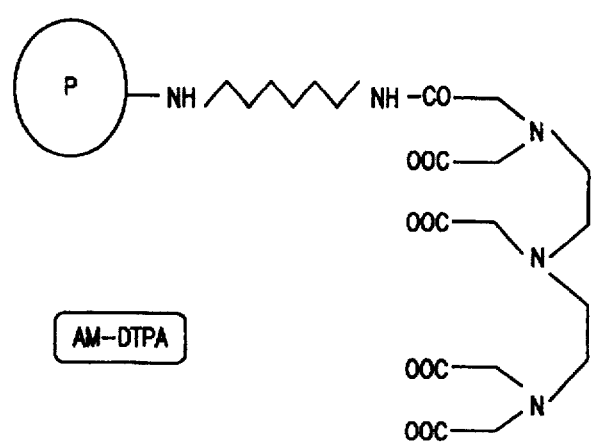
Figure 4:
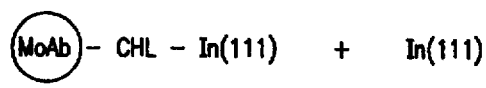
Figure 4:
Figure 4:
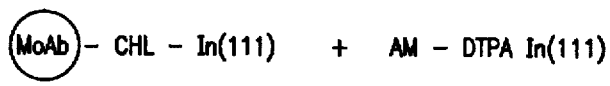

FIG. 4 is another embodiment wherein beads and chelator are coupled directly. Alkylamine derivatized particulate polymer matrix (p-NH . . . ) is conjugated with DTPA dianhydride to form AM-DTPA. In a fashion similar to that depicted in FIG. 3, AM-DTPA scavenges In(111) from the reaction mixture. In place of the chelator DTPA, IDAC-2 may also be used.

To further minimize non-specific binding to the matrix, the conjugates can be exposed to proteinaeous or carbohydrate material to block those non-specific sites. Suitable blocking agents include bovine serum albumin, human serum albumin, sera, polyvinylpyrrolidone, dextran and ficoll. The chelator-matrix conjugates are washed thoroughly and an appropriate quantity is charged into a first vessel or into a chamber of said multiple-chambered vessel.

The biomolecule is conjugated with a chelating agent, preferably the same species as that conjugated to the matrix. Following the conjugation step, the biomolecule is separated from the unconjugated chelating agent by, for example, precipitation or gel exclusionchromotography. The resulting solution is charged into a second vessel or into a separate chamber of said multiple-chambered vessel. The labeling reagent, which is generally purchased from commercial vendors, is then introduced into the biomolecule-containing solution and chelation is allowed to proceed under appropriate incubation conditions. In the next step, the labeling reaction solution is removed to the vessel or chamber containing the chelator-matrix conjugate. The final mixture is incubated with periodic mixing. The supernatant containing the labeled biomolecule is removed.

Alternatively, the biomolecule, which serves as the effector molecule, for example, an antibody or nucleic acid probe, need not be labeled with an agent that in itself is detectable. Instead, the effector molecule is labeled with a first binding partner molecule and the detectable labeling agent is conjugated to a second binding partner molecule, wherein said first and second binding partner molecules react with each other to form a conjugate. The alternative labeling method is known as pretargeting. For example, tissue-reacted streptavidin-conjugated antibody may be visualized using radiolabeled biotin, and a hybridized nucleic acid probe containing a poly-A tail may be visualized with an alkaline phosphatase conjugated poly-T oligonucleotide and an appropriate phosphatase substrate such as NBT/BCIP. In the first antibody example streptavidin and biotin are the first and second binding partner molecules, and in the second nucleic acid example poly-A and poly-T polynucleotides are the first and second binding partner molecules. Polymers that may be used as binding partner molecules include poly-N-vinylpyrrolidone, polyvinyl alcohols, polyethylene oxide and poly-N-vinylpyridine, which react with polyacrylic acids and polymethacrylic acids.

The following non-limiting examples further illustrate and show aspects of the instant invention.

EXAMPLE 1

Polystyrene beads were conjugated with DTPA in a two-step method. Human serum albumin (HSA) in 50 mM phosphate-buffered saline, pH 7.2, was incubated with a 100-fold molar excess of DTPA dianhydride at room temperature for 15 minutes. Unconjugated DTPA was removed by passing the mixture over a G-50 column.

The HSA-DTPA solution was adjusted to 14 mg/ml and about 40 quarter inch, spherical, non-porous beads were added to the solution. The mixture was incubated with gentle shaking at room temperature for 2 hours. The liquid was decanted, the beads were washed with distilled water and dried under vacuum.

EXAMPLE 2

A 0.1 mg/ml solution of DTPA anhydride in dry chloroform was prepared and an aliquot containing the desired quantity of DTPA was added to a reaction vessel. The chloroform was removed by evaporation with nitrogen gas at room temperature. A pH 7.0 solution of antibody (approximately 0.5 mg) in 0.05M bicarbonate buffer was added to said reaction vessel to produce a 7:1 molar ratio of anhydride to protein. The solution was incubated with shaking for one minute and the coupled antibody was recovered by passage over a Sephadex G-50 column.

EXAMPLE 3

The radionuclide was made 0.5M in acetate, using 1.0M acetate, with a final pH of 6.0. The radionuclide solution was added to the antibody-DTPA conjugate along with 0.1 ml of 25% human serum albumin and the mixture was incubated for 5–30 minutes with frequent stirring.

EXAMPLE 4

HSA-DTPA beads were added to a solution containing $^{111}$In in acetate/citrate buffer in a total volume of 0.75 ml for about 30 minutes. The solution was removed and the radioactivity bound to the beads was determined.

| Number of Beads | Radioactivity in μCi |
|---|---|
| 5 | 22 |
| 12 | 30 |
| 20 | 62 |

There is a direct correlation between the number of beads and the amount of bound reactivity. Also, washing the beads with 1M HCl removed all bound radioactivity, enabling the beads to be reused.

EXAMPLE 5

HSA-DTPA was labeled with $^{111}$In in citrate/acetate buffer as described above. An aliquot was removed and treated with excess DTPA. Said DTPA-treated aliquot was analyzed by thin layer chromatography to determine percent free $^{111}$In. The aliquot contained 12.2% free $^{111}$In. Five HSA-DTPA beads were added to the HSA-DTPA-$^{111}$In solution and the mixture was incubated at room temperature for 30 minutes. An aliquot was removed from that mixture, treated with excess DTPA and analyzed by TLC for free $^{111}$In. Said second aliquot contained 3.9% free $^{111}$In.

EXAMPLE 6

LiLo is a novel chelator described in U.S. Pat. No. 5,292,868, issued Mar. 8, 1994, which is included herein by reference. The chelator was attached to amine derivatized (AM) beads by exposing 60 AM beads to 5 ml of a saturated solution of LiLo prepared in water or in phosphate-buffered saline, pH 7.2. The pH of the mixture was adjusted to 7.5–8.5 using NaOH. The solution was stirred overnight at room temperature. The liquid was decanted and 1M HCl was added to the beads. The mixture was incubated at room temperature for 10 minutes. That step removed free metal bound to LiLo-conjugated AM beads. The beads were rinsed repeatedly with 0.1M HCl. That was followed by distilled water rinses until the wash was neutral to pH paper. The beads were dried under vacuum and stored in a desiccator.

EXAMPLE 7

Two hundred microcuries of indium chloride were combined in an acid-washed reaction vial with 15 μl of acetate buffer (0.6M, pH 5.5) and 15 μl of citrate buffer (0.06M, pH 5.5). Antibody-DTPA conjugate (157 μg in phosphate-buffered saline, pH 7.2) was added to the solution and the mixture was incubated at room temperature for about 30 minutes. Then, about 1 ml of phosphate-buffered saline (0.05M, pH 7.2) was added. An aliquot of the reaction mixture was treated with excess DTPA solution to determine the percentage of unbound Indium-111 in the reaction mixture. To the remaining reaction solution, eight AM-LiLo beads were added. After incubating with the beads for about 30 minutes, an aliquot of the reaction solution was treated with excess DTPA. A chromatographic analysis was carried out to determine the percentage of unbound Indium-111 with the following results:

| Method | Percentage of Indium-111 bound to the antibody |
|---|---|
| Before beads | 83% |
| After beads (AM-LiLo) | 99.7% |

EXAMPLE 8

Synthesis of IDAC-2

Figure 5:
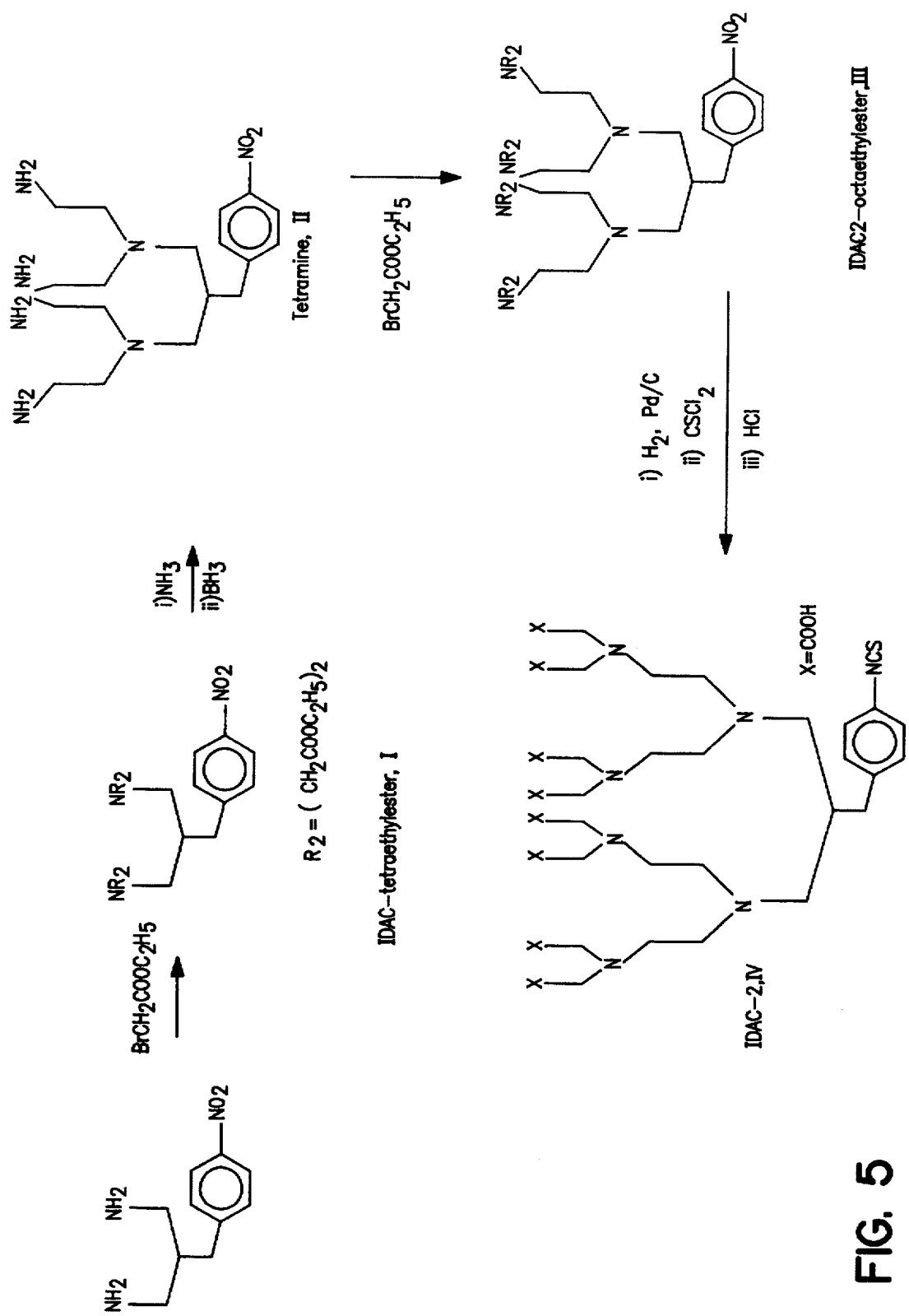
FIG. 5 depicts a synthesis route for preparing IDAC-2.

IDAC-2, the bifunctional chelate suitable for attaching radiometals to proteins, is prepared from tetramine (II) as illustrated in FIG. 5.

Synthesis of IDAC tetraethylester (I) has been described in U.S. Pat. No. 5,204,448 (FIG. 2B, compound XI), which is included herein by reference. The tetramine derivative (II) needed for the preparation of IDAC-2 is obtained from IDAC ester by first synthesizing a tetramide derivative using ammonia, followed by reduction with borane in tetrahydrofuran (FIG. 5).

Tetramide derivative: 14.7 g of IDAC tetraethylester (I) were dissolved in approximately 500 ml of methanol. Ammonia gas was bubbled through the solution to the point of saturation. The vessel was then stoppered and placed in the refrigerator. After about 1 hour the solution was saturated again with ammonia. The solution was then rotoevaporated to dryness.

Tetramine (II): 500 ml of 1M borane-tetrahydrofuran complex were added to a solution of the tetramide derivative in 300 ml of tetrahydrofuran. The solution was heated to reflux for about 48 hours, after which THF was evaporated. Concentrated HCl was added dropwise to quench excess borane. HCl was then added (100 ml) and the solution heated to reflux. This was followed by the evaporation of the solution to dryness. To the dry powder obtained, methanol was added and rotoevaporated. This procedure was repeated twice.

Synthesis of IDAC-2-octaethylester (III): 25 ml of ethylbromoacetate were added to the tetramine (II) sample obtained above in 400 ml of acetonitrile. The solution was heated to reflux. This was followed by stirring at room temperature. The reaction mixture was rotoevaporated and purified further using silica gel chromatography.

Synthesis of IDAC-2 (IV): IDAC-2 was obtained from IDAC-2-octaethylester (III) by first converting the nitro derivative into an aminobenzyl IDAC-2-octaethylester derivative using Pd/H$_2$, and then to an isothiocyanatobenzyl IDAC-2-octaethylester derivative using thiphosgene. IDAC-2 was obtained from the isothiocyanato derivative of IDAC-2-octaethylester by acid hydrolysis (R. Subramanian et al., Bioconjugate Chemistry, 3, 248–255, 1992).

IDAC-2: 2 g of IDAC-2-octaethylester (III) were dissolved in approximately 15 ml of methylene chloride and the solution was added to a stirring solution of 10% palladium on carbon (approximately 300 mg) in ethanol bubbled with hydrogen gas. The reaction was allowed to occur for about 6 hours with continuous bubbling of nitrogen gas. The reaction solution was filtered at the end and rotoevaporated to get (4-aminobenzyl)IDAC-2-octaethylester.

(4-aminobenzyl)IDAC-2-octaethylester was dissolved in approximately 100 ml of methylene chloride, and 2 ml of thiophosgene were added to the solution with stirring. The solution was stoppered under a nitrogen atmosphere and left to stir at room temperature. Approximately 20 ml of methanol were added and the solution was stirred for an additional 15 minutes. The product was then rotoevaporated. The resulting oil was dissolved in methylene chloride and saturated sodium carbonate solution and shaken well. The solution was then extracted with methylene chloride, dried over magnesium sulfate, filtered and rotoevaporated. This solution was run down a silica gel column. Fractions containing (4-isothiocyanatobenzyl) IDAC-2-octaethylester were combined and rotoevaporated. To 1.78 g of (4-isothiocyanatobenzyl) IDAC-2-octaethylester obtained as above, 4 ml of concentrated HCl and 40 ml of water were added and shaken well. This was left to sit at room temperature to give IDAC-2 (yield 1.41 g).

EXAMPLE 9

Preparation of 16.88-IDAC-2: A typical conjugation procedure is as follows: In a reaction tube 16.88 (10.4 mg/mL, 2 mL) and IDAC-2 (100 mg/mL, 0.04 mL) solutions were combined and the pH of the solution was adjusted to 8–9. The reaction mixture was incubated at 37° C. for about 2 hours. At the end, the reaction mixture was purified by gel filtration chromatography using Sephadex G50 gel. The absorbances of the fractions were measured at 280 nm using a UV/VIS spectrophotometer. The immunoconjugate 16.88-IDAC-2 eluted off the column in the first peak.

In-111 Labeling of 16.88-IDAC-2: A typical radiolabeling reaction is as follows: To approximately 0.3 mCi of indium-111 chloride, 15 uL of 0.6M sodium acetate, pH 5.5, and 0.06M sodium citrate, pH 5.5, solutions were added. This solution mixture was combined with 0.12 mL of 16.88-IDAC-2 solution (0.3 mg) and the radiolabeling reaction was allowed to occur at room temperature for about 1 hour. At the end of the reaction an aliquot of DTPA solution (0.5 to 1 mM) was added to the reaction mixture to bind free indium-111. The reaction mixture was further purified using Sephadex gel filtration chromatography. The radiolabeled antibody eluted off the column in the first peak.

Stability studies of the radiolabeled antibody were performed in the presence of excess of DTPA solution and the analysis was carried out by thin layer chromatography.

We claim:

1. A chelating agent IDAC-2 having the formula:

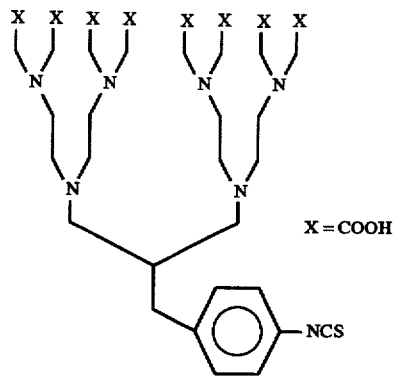

2. A conjugate comprising a polypeptide bound to the chelating agent IDAC-2 of claim 1.

3. A complex comprising a radionuclide bound to the chelating agent IDAC-2 of claim 1.

4. A complex comprising a metal bound to the chelating agent IDAC-2 of claim 1.

5. The conjugate of claim 2, wherein the polypeptide is an antibody.

6. The conjugate of claim 2, comprising a metal bound to the chelating agent IDAC-2.

7. The conjugate of claim 6, wherein the metal is a radionuclide.

* * * * *